United States Patent
Barlow et al.

(10) Patent No.: US 6,926,429 B2
(45) Date of Patent: Aug. 9, 2005

(54) EYE TRACKING/HUD SYSTEM

(75) Inventors: R. Michael Barlow, Southfield, MI (US); Joseph E. Harter, Jr., Kokomo, IN (US); Gregory K. Scharenbroch, Kokomo, IN (US); Timothy J. Newman, Noblesville, IN (US)

(73) Assignee: Delphi Technologies, Inc., Troy, MI (US)

( * ) Notice: Subject to any disclaimer, the term of this patent is extended or adjusted under 35 U.S.C. 154(b) by 744 days.

(21) Appl. No.: 10/059,070

(22) Filed: Jan. 30, 2002

(65) Prior Publication Data

US 2003/0142041 A1 Jul. 31, 2003

(51) Int. Cl.[7] .............................. G09G 5/00; G01D 11/28
(52) U.S. Cl. ..................... 362/464; 362/503; 362/276; 345/7; 340/576; 359/630
(58) Field of Search ................... 362/503, 464, 362/276, 466, 802; 345/7, 8, 9; 340/576, 425.5; 382/118, 117, 115; 359/269, 630, 634, 632

(56) References Cited

U.S. PATENT DOCUMENTS

| | | | |
|---|---|---|---|
| 4,625,329 A | * 11/1986 | Ishikawa et al. | 382/104 |
| 5,237,455 A | 8/1993 | Bordo et al. | 359/632 |
| 5,320,534 A | * 6/1994 | Thomas | 345/8 |
| 5,408,346 A | * 4/1995 | Trissel et al. | 349/115 |
| 5,414,439 A | * 5/1995 | Groves et al. | 345/7 |
| 5,729,619 A | 3/1998 | Puma | |
| 5,856,811 A | 1/1999 | Shih et al. | 345/8 |
| 6,087,941 A | 7/2000 | Ferraz | |
| 6,097,295 A | 8/2000 | Griesinger et al. | |
| 6,437,759 B1 | * 8/2002 | Turner et al. | 345/8 |
| 6,447,132 B1 | * 9/2002 | Harter, Jr. | 362/29 |
| 6,750,832 B1 | * 6/2004 | Kleinschmidt | 345/7 |

FOREIGN PATENT DOCUMENTS

JP         03042337          2/1991

* cited by examiner

Primary Examiner—John Anthony Ward
Assistant Examiner—Bao Q Truong
(74) Attorney, Agent, or Firm—Stefan V. Chmielewski

(57) ABSTRACT

In a preferred embodiment, an apparatus for eye tracking, including: an illuminator; reflection apparatus to reflect illumination from the illuminator onto a surface of a windshield of a vehicle in which the windshield is installed, such that the illumination is reflected onto at least an eye of a person in the vehicle, and to reflect an image of the at least an eye, and a sensor to receive a reflection of the image of the at least an eye reflected by the reflection apparatus and to produce an output signal representative thereof.

9 Claims, 5 Drawing Sheets

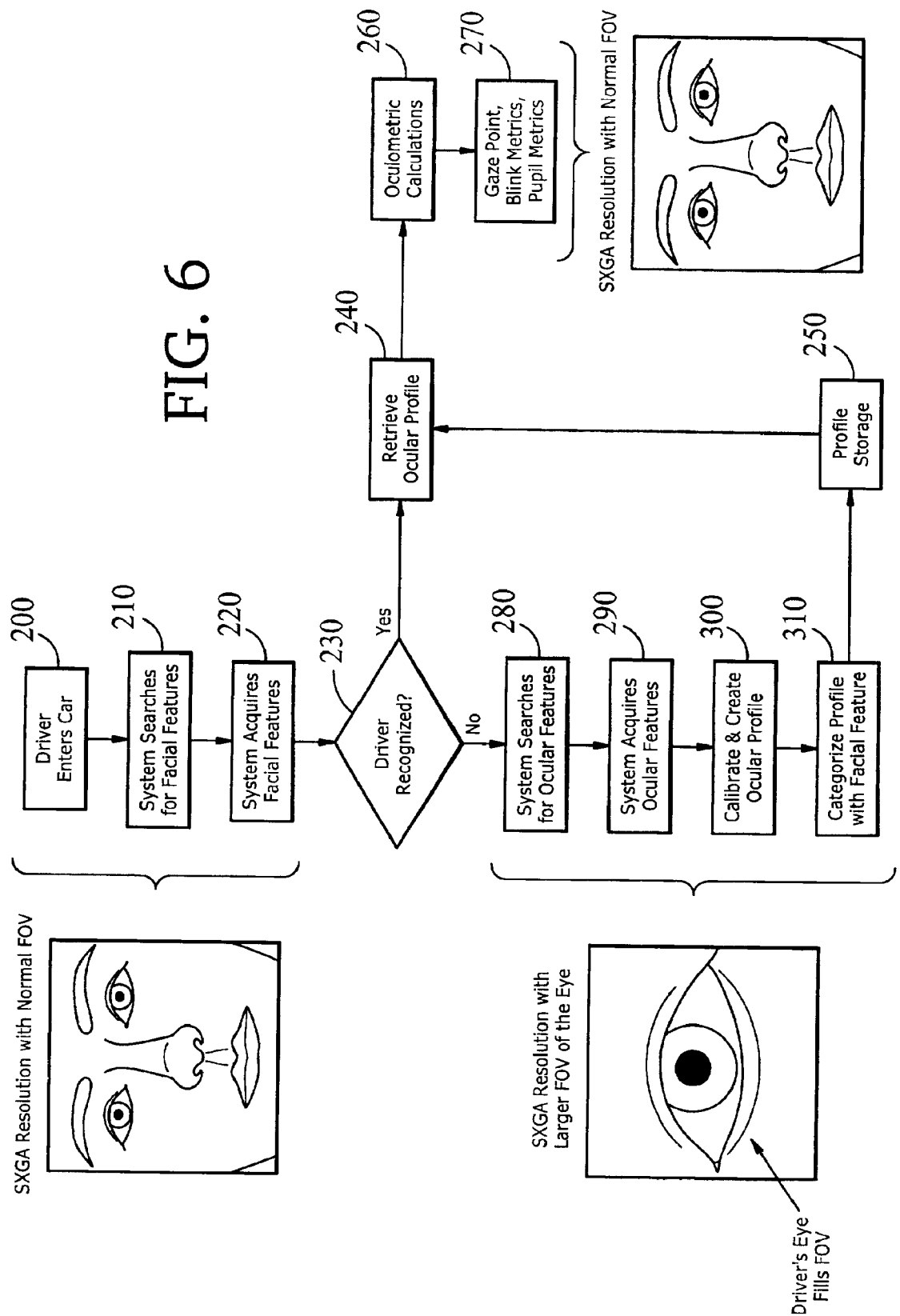

EYE TRACKING/HUD SYSTEM

BACKGROUND OF THE INVENTION

1. Field of the Invention

The present invention relates to eye tracking systems generally and, more particularly, but not by way of limitation, to a novel eye tracking system using, in part, an existing head up display (HUD).

2. Background Art

While the present invention is described generally in the context of determining inattentiveness of the driver of a vehicle, it will be understood that the invention is application, as well, to any situation in which tracking of eye movements is desirable. Communities in which eye tracking is used include the medical, research, and academic communities where eye tracking is useful, for example, in determining psychological response and how a person scans.

A large number of the approximately 35,000 vehicular deaths and a much larger number of vehicular accidents each year in the United States can be attributed to driver inattention. Driver inattention may result from drowsiness, use of a telephone, use of a computer, changing stations on a radio, conversing with another occupant of the vehicle, and similar causes. Whatever the cause, such driver inattention may result in fatalities and non-fatal accidents.

In response to this problem, systems have been developed to continuously track an eye of a driver and use this information to determine when the driver becomes inattentive and to institute measures to alert the driver of the potential disaster. Eye tracking can be an accurate, non-intrusive, non-contact method, which detects driver inattention and fatigue by recording eye movement. Parameters such as blink duration, blink frequency, and eye closure can be useful for detecting drowsiness, fatigue, and other causes of inattentiveness. Pupillary data such as diameter, shape, location, and rate of change can be useful in determining the direction of the driver's gaze and workload. Thus, it is a key safety system that can be used to determine the state of the driver for workload management systems.

Although there are a number of eye tracking methods, many are quite expensive and many involve undesirable intrusiveness, both undesirable features for a vehicular system. Some of these methods are discussed below.

The limbus eye tracking method utilizes the difference in reflectance between the sclera and the iris. The reflectively difference produces a contrast that can be monitored by photodetectors mounted on either side of the eyeball. This method requires head mounted sensors and, when used alone, is sensitive to head movement when calculating gaze.

The pupil tracking method is similar to the limbus tracking method, except that it uses the boundary between the pupil and iris, rather than the boundary between the sclera and the iris. This method is advantageous in that the pupil is far less covered by the eyelid than is the limbus and the border is sharper than that of the limbus, thus offering a higher resolution. A disadvantage is that the contrast is lower.

The cornea/pupil relationship method may be one of two types. In dark pupil tracking, collimated, on-axis IR illumination causes a dark pupil to appear bright. The high contrast with the dark pupil acts as a light sink. In bright pupil tracking, uncollimated, off-axis IR illumination reflects off the retina similar to the reflection seen from the eyes of a nocturnal animal or in red-eye from flash photography. In either case, a CCD or CMOS detector is used. Pupil edge is located and the center is calculated.

The artificial neural network method uses brain waves and artificial intelligence in software to calculate alertness, etc Capturing the brain waves requires the use of electrodes placed on the scalp or placing the subject in an MRI type of device.

The dual Purkinje image method compares the corneal reflection to the reflection from the back surface of the lens. Measurements are made of the relative displacement between the first and fourth reflections, to the shape and size of the pupil, which represent the focal point. Because the IR illumination has to travel through seven interfaces, the method is very inefficient and requires a relatively powerful illumination source.

The electro-oculographic method calculates eye position by measuring the potential difference between the front and back of the eyeball. This method is simple, but not reliable, due to signal variations over time, and not precise, due to noise levels. Of course, electrodes must be placed around the eye.

The search coil method requires that induction coils be embedded in the sclera or in tight fitting contact lenses. This is a very accurate method, but also quite intrusive.

The video-oculographic method gives an accurate measurement of eye components, including ocular torsion. The method also provides pupil diameter measurement and monocular and binocular measurement with pupil diameter. There is no drift and reduced noise sensitivity As noted above, the foregoing methods are unsuitable for vehicular use because of cost and/or intrusiveness, although some produce fairly accurate results.

Commonly, a system used in vehicular eye tracking includes one or two IR sources directed at an eye of the driver, a combination of mirrors and motors, an eye camera module, and a processing and control unit. As the two light sources shine on an eye, two spots (invisible, but seen by the infrared camera) occur in the pupil. The eye camera module captures and sends an image of the eye to the processing and control unit, which calculates the direction of driver gaze by comparing the locations of the two spots in the pupil. The mirror/motor combination is used in front of the eye camera adjusts to try to track the driver's eye as the driver's head is moved and also adjusts to driver height through calibration. This requires a complex and expensive auto focus and tracking system.

One problem is that such current eye tracking systems use a small field of view lens to cover a small area around the eye of the driver and an image sensor having a sub-QVGA ("quarter video graphic array) resolution (or one-quarter of the standard 640×480 VGA pixelation). Because of these limitations, conventional eye tracking systems permit only limited head movement. If the limited degree of head movement is exceeded by sudden head movement, head rotation, or vibration, for example if the vehicle runs on a rocky road, the system will "lose" the eye and becomes ineffective until the eye can again be tracked which can take some time.

Another problem with such current eye tracking systems is that, since each person has a slightly different ocular profile that can result in a large error in calculation, the eye tracking system needs to be calibrated for each different driver. This is done by having the driver sit still in the driver's seat while an instructor sits in the front passenger seat. The instructor tells the driver to took at a particular spot, or fixate on predetermined alignment coordinates, for a short period of time. The instructor then measures and records oculometric data. This procedure is repeated some six or nine times. Then, the instructor takes the recorded data and develops an ocular profile of the driver that is recorded in a look-up table that is manually accessed for each driver. This must be done for each potential driver of the vehicle. In addition to the fairly tedious start-up procedure, periodic recalibration is required because of drift.

In addition to the above problems, the use of electromechanical components inherently renders a system complex and relatively costly and introduces additional areas in which alignment is critical and in which the wearing of mechanical linkages eventually introduces additional errors into the eye tracking system.

A further disadvantage of conventional eye tracking systems is that placement of a detector in a vehicle becomes a problem. One reason for this is that the path from the drivers' eye to the detector cannot become obstructed, for example, by the driver's hands. It would also be desirable to utilize some of existing systems in a vehicle. It is also desirable that the driver's field of view not be obstructed.

Accordingly, it is a principal object of the present invention to provide an eye tracking system that has no moving parts.

It is a further object of the invention to provide such an eye tracking system that can increase the field of view to well beyond the area around the eye, while maintaining adequate resolution.

It is an additional object of the invention to provide such an eye tracking system that is automatically calibrated for each driver.

It is another object of the invention to provide such an eye tracking system that permits nearly 180° head rotation, while continuing to monitor an eye.

It is yet a further object of the invention to provide such an eye tracking system that includes automatic driver identification.

It is yet an additional object of the invention to eliminate or greatly reduce the potential for "lost" eye contact.

It is yet another object of the invention to provide such an eye tracking system that uses high resolution methods to examine the entire face of a driver and retrieve and ocular profile based on the identification of the driver or to prepare and store an ocular profile, using a high resolution image of an eye, if the driver is not recognized.

Yet a further object of the invention is to provide such an eye tracking system that utilizes portions of an existing system in a vehicle Yet an additional object of the invention is to provide such an eye tracking system that does not obstruct the driver's field of view.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, an apparatus for eye tracking, comprising, an apparatus for eye tracking, comprising an illuminator; reflection means to reflect illumination from said illuminator onto a surface of a windshield of a vehicle in which said windshield is installed, such that said illumination is reflected onto at least an eye of a person in said vehicle, and to reflect an image of said at least an eye; and a sensor to receive a reflection of said image of said at least an eye reflected by said reflection means and to produce an output signal representative thereof.

BRIEF DESCRIPTION OF THE DRAWING

Understanding of the present invention and the various aspects thereof will be facilitated by reference to the accompanying drawing figures, provided for purposes of illustration only and not intended to define the scope of the invention, on which

FIG. 6 is a logic flow diagram of the system of the present invention.

DETAILED DESCRIPTION OF THE PREFERRED EMBODIMENTS

Figure 1:
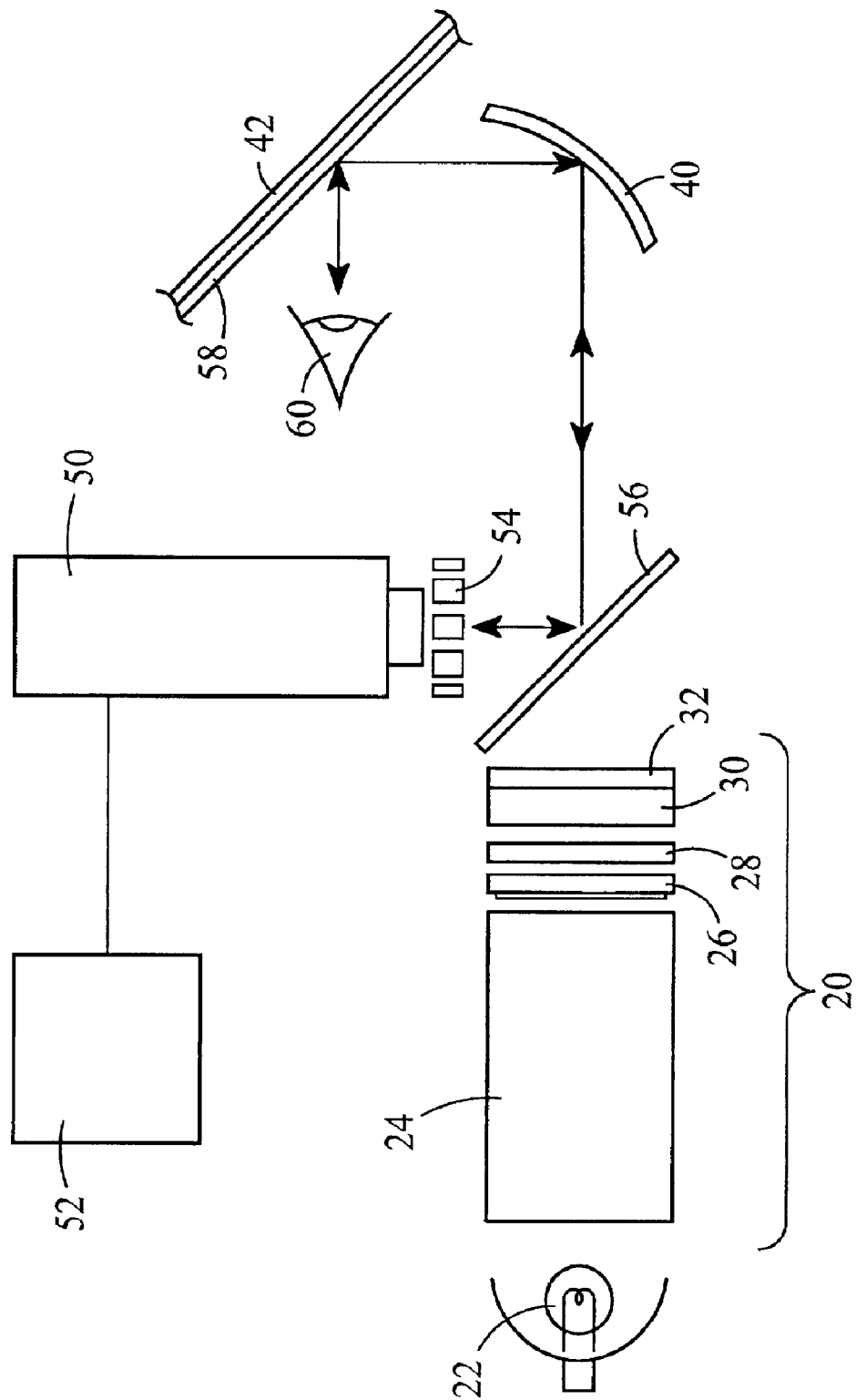
FIG. 1 is schematic view of an eye tracking system according to the present invention used to track the eye movements of a person.

Reference should now be made to the drawing figures on which similar or identical elements are given consistent identifying numerals throughout the various figures thereof, and on which parenthetical references to figure numbers direct the reader to the view(s) on which the element(s) being described is (are) best seen, although the element(s) may be seen on other figures also.

FIG. 1 illustrates the present invention incorporated in an head up display (HUD) system. The conventional elements of the HUD include an engine 20 having a backlight source 22, an optical coupler 24, a polarizer/substrate 26, a diffuser 28, an a display device 30 having thereon a polarizing optical film 32, all the elements being arranged as shown on FIG. 1. HUD engine 20 projects an image that is reflected by an aspheric mirror 40 onto a vehicle windshield 42. This image may include any information that is to be imparted to the driver of the vehicle, such as vehicle speed, distance to or from a location, etc. The image is viewed by the driver without obstruction of the driver's view through the windshield.

The present invention adds the elements of an IR sensor/camera 50 that provides an input to a processing platform 52, a ring of IR illuminators 54 disposed near the IR sensor/camera 50, and an IR mirror 56 that reflects radiation from the IR illuminators onto aspheric mirror 40. Aspheric mirror 40, in turn reflects the radiation onto windshield 42 which may have an IR reflection enhanced surface 58. The radiation reflects off surface 58 and showers an eye 60 and the face (not shown on FIG. 1) of the driver. The resulting image of the eye and face of the driver is reflected in sequence off surface 58, aspheric mirror 40, and IR mirror 56 and is received by IR sensor/camera 50 The signal from sensor/camera 50 is passed to processing and control circuitry in processing platform 52 and used in the manner described below, the processing and control circuitry also controlling the other elements of the system IR sensor/camera 50 could include electronic pan tilt to compensate for head and eye movement Illumination sources other than IR may be provided, as long as the other illumination sources are non-intrusive. The system 10 has no moving parts.

Figure 2:
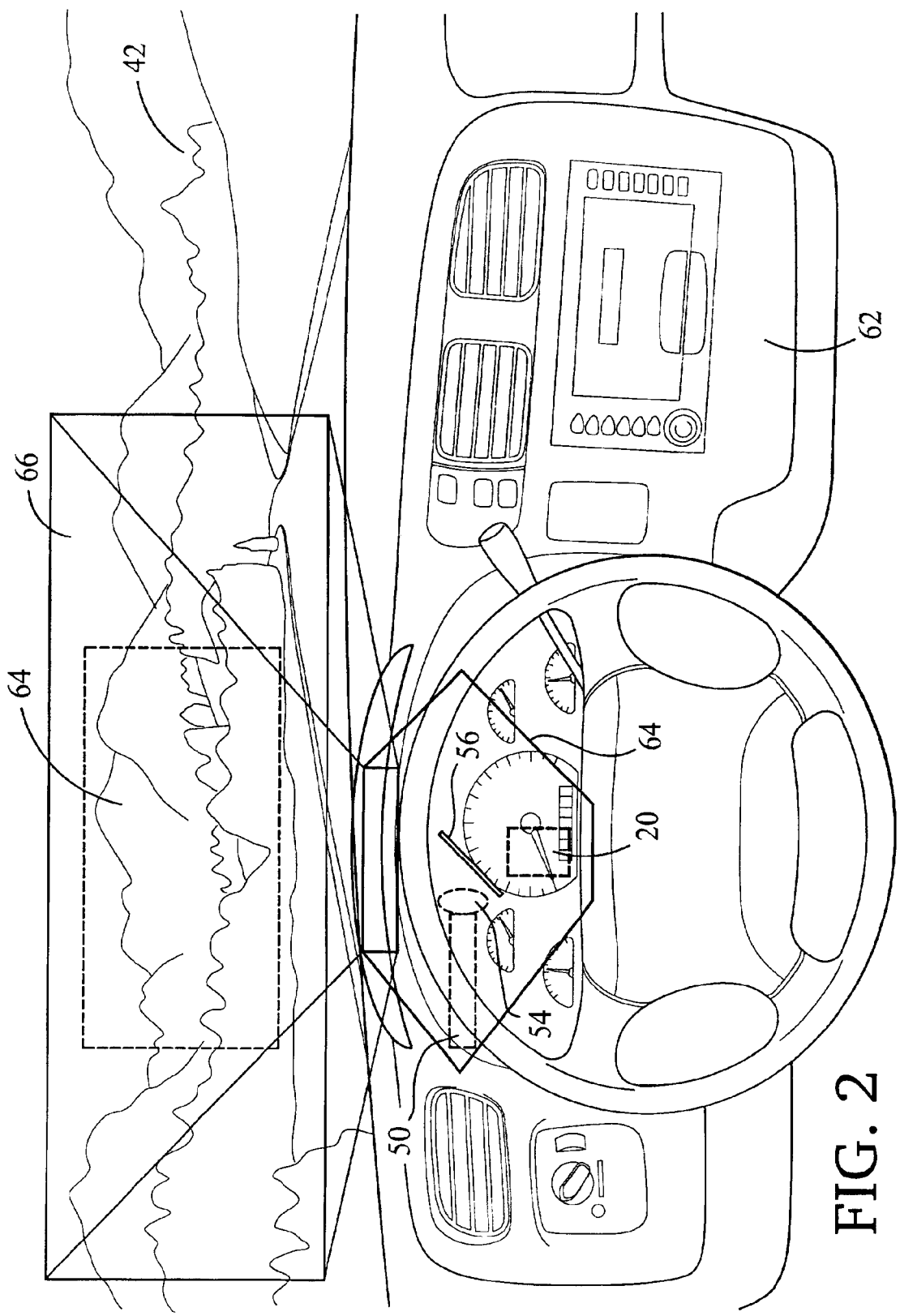
FIG. 2 is a partially schematic view of a dashboard and windshield of a vehicle in which the present invention is installed.

FIG. 2 illustrates some of the elements shown on FIG. 1 installed in a dashboard 62 of a vehicle (not otherwise shown), including IR sensor/camera 50, IR illuminators 54, IR mirror 56, HUD engine 20 (in a HUD unit 64). FIG. 2 also shows an area 64 representing the HUD "eyebox" and an area 66 representing a larger area that is the area of the field of detection of the driver's gaze or facial features. It will be understood that the optical elements of the present invention can be disposed such that there is little chance of obstruction of the line of sight between the optical elements. Also, the system is non-invasive.

The conventional, low-resolution CCD sensor in sensor/camera 50 has been replaced in this invention with a high-resolution CMOS device, which permits a larger field of view, while maintaining the minimum required pixel density for precise oculometric data acquisition and permits increased freedom of head movement. This change increases the resolution of the optical from the conventional sub-QVGA to high resolution such as SXGA (1280×1024 pixels) Now, the entire face of the user can be viewed, permitting the use of known techniques to extract facial features after suitable image processing. This results in the 8–10 pixels per degree that is achieved with conventional systems that view only the eye of the driver.

Figure 3:
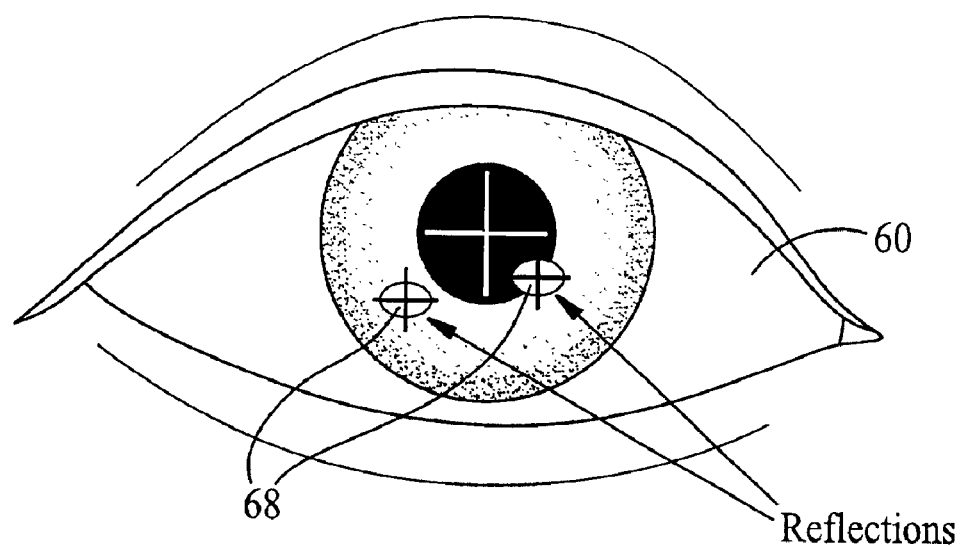
FIG. 3 shows the reflections of IR sources in an eye.

The facial feature extraction enables the system to recognize the driver of whom the oculometric profile is stored and uploaded quickly. This then eliminates the need for annoying recalibration for different learned drivers, as well as expedites the learning process. Facial feature extraction also enables auto-calibration by the use of search and recognition algorithms to determined eye location and its associated oculometric geometry within the system Facial feature extraction can also be used to determine how the vehicle can be operated or access to various areas of the vehicle. For example, if the driver is not recognized, the operating system may go into "valet mode" in which certain areas of the vehicle, such as the glove compartment or the trunk of the vehicle cannot be accessed by the driver FIG. 3 illustrates the reflections 68 of IR illuminators 54 (FIG. 1) in the eye 60 of a driver. It will be understood that the reflections shown on FIG. 3 are for illustrative purposes only and that the reflections would not be visible. This is an example of a non-contact technique that uses the pupil/cornea reflection principle. The positions of the pupil and reflex centers are determined from a digitized video image and the driver's point of gaze is determined by calculating the difference vectors of reflections 68.

Figure 4:
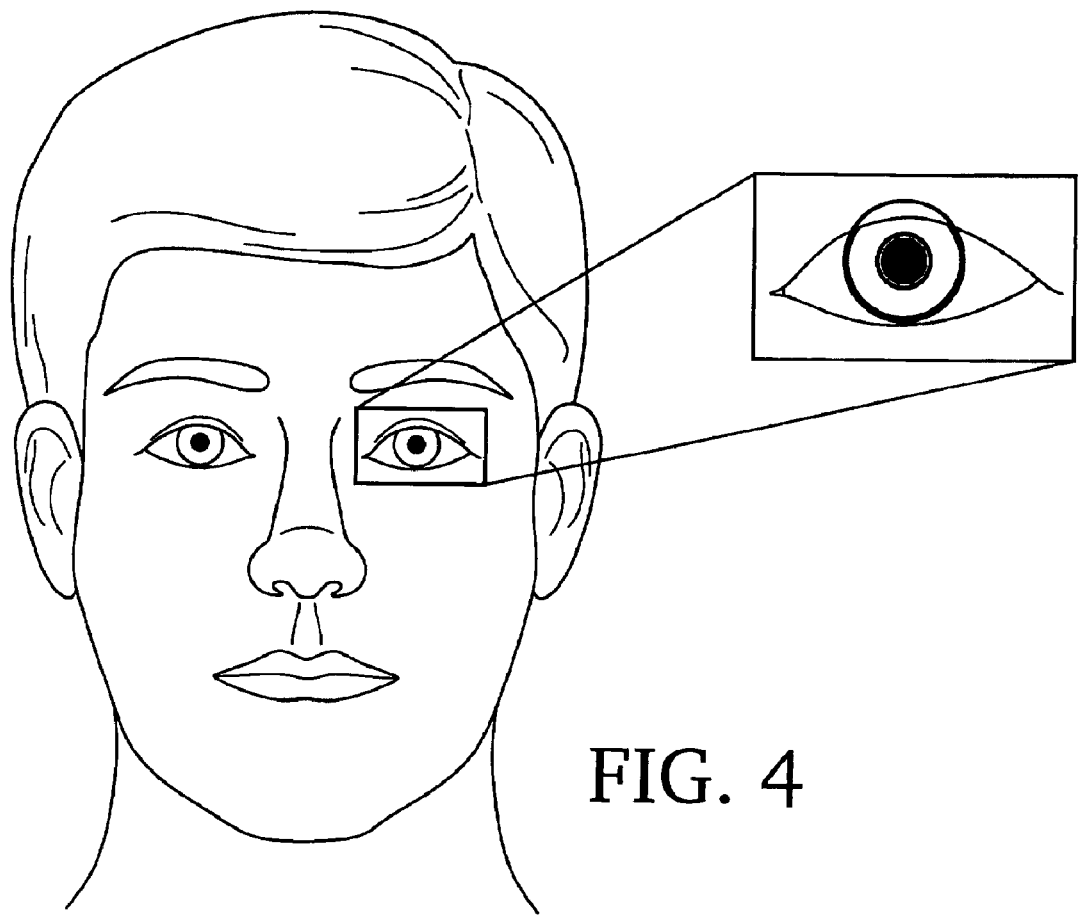
FIG. 4 shows a full face view and a view of an eye as used in the present invention.

FIG. 4 illustrates the full face view and an eye view as used by the system, the use of which is described below.

Figure 5:
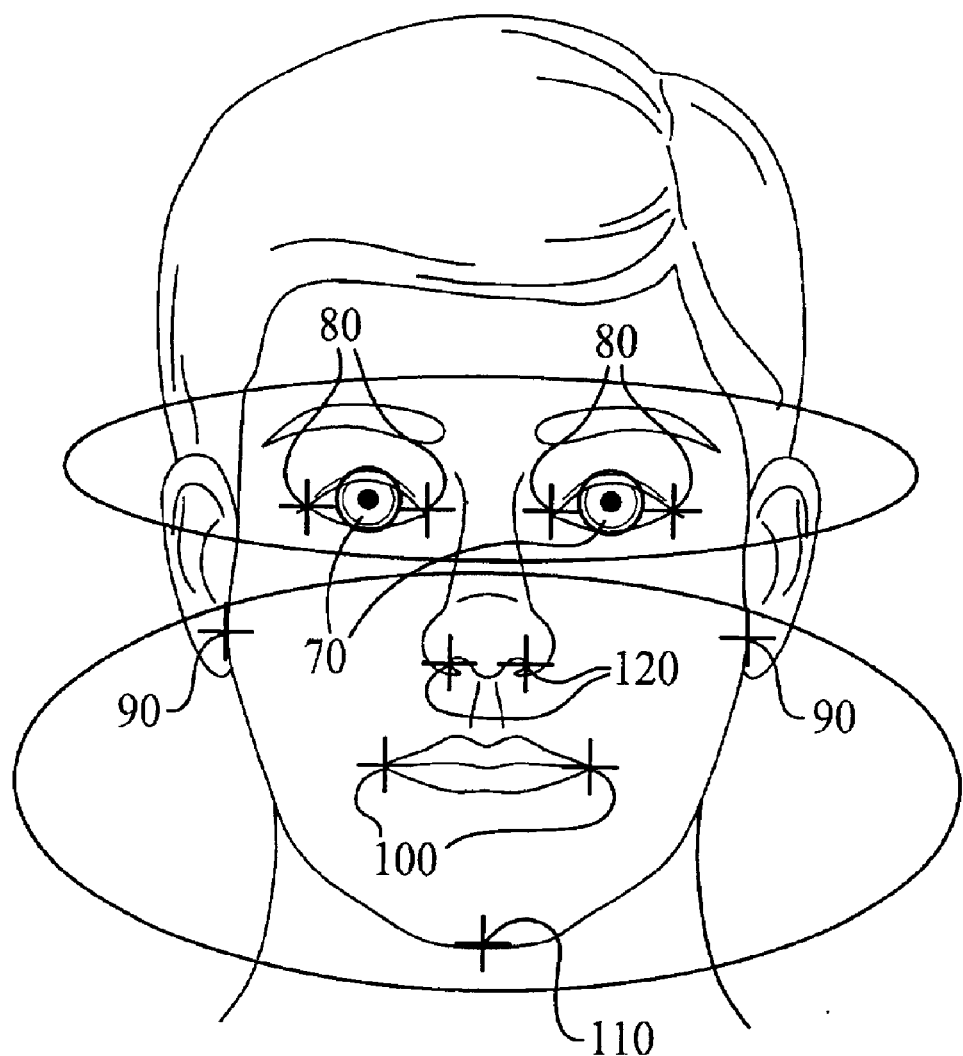
FIG. 5 shows various features that may be used by the present invention to identify a driver.

FIG. 5 illustrates facial features that may be used to identify a driver. These include the positions and sizes of the eyes 70, the corners 80 of the eyes, the ears 90, the corners 100 of the mouth, the chin 10, and the ala 120, of the nose.

Initial calibration now requires only that a driver sit in the driver's seat. The system automatically scans the face of the driver and stores identifying information in memory. Now, when the same driver sits in the driver's seat, the system scans the face of the driver, recognizes the driver and automatically uploads the driver's profile, eliminating the need to re-calibrate for different drivers. This profile can also be used to identify the driver and load stored presets. Of course, portions of the system may be overridden if, for example, the vehicle is to be given to a parking valet.

FIG. 6 is a logic flow diagram illustrating the operation of the system.

First, using SXGA resolution, the whole face of a driver constitutes the field of view. The driver enters the vehicle at step 200. At step 210, the system searches for particular facial features. At step 220, the system acquires the facial features of the driver (FIG. 5). At step 230, the system determines if the driver is recognized. If the driver is recognized, the driver's ocular profile is retrieved at step 240 from profile storage 250. This is used at step 260 to perform oculometric calculations. At step 270, oculometrics are determined while continuing to use the whole face of the driver in the field of view.

If the driver is not recognized at step 230, the system uses SXGA resolution in which an eye of the driver fills the entire field of view and, at step 280, the system searches for ocular features At step 290, the system acquires the ocular features. At step 300, the system calibrates and creates an ocular profile. The ocular profile created at step 300 is then categorized at step 310 with the facial features acquired at step 220 and the ocular profile is stored in the profile storage 250.

At the foregoing steps are automatic and require no manual input on the part of the driver or any other person.

Should eye contact be "lost", by the driver completely moving the driver's head, for example, the system goes into standby mode until a face is recognized, with the system using the whole face in the field of view. Then, knowing where the eye being tracked is located on the face, the system can again use the ocular profile to perform oculometric calculations. The system differentiates between a normal blink and the loss of data.

In the embodiments of the present invention described above, it will be recognized that individual elements and/or features thereof are not necessarily limited to a particular embodiment but, where applicable, are interchangeable and can be used in any selected embodiment even though such may not be specifically shown. Terms such as "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

What is claimed is:

1. An apparatus for eye tracking, comprising:
   (a) an illuminator;
   (b) reflection means to reflect illumination from said illuminator onto a surface of a windshield of a vehicle in which said windshield is installed, such that said illumination is reflected onto at least an eye of a person in said vehicle, and to reflect an image of said at least an eye; and
   (c) a sensor to receive a reflection of said image of said at least an eye reflected by said reflection means and to produce an output signal representative thereof.

2. An apparatus for eye tracking, as defined in claim 1, wherein: said reflection means is at least part of a head up display in said vehicle.

3. An apparatus for eye tracking, as defined in claim 1, further comprising:
   (a) a controller operatively connected to said sensor to receive said output signal;
   (b) said controller configured to cause said sensor to view an entire face of said person to obtain predetermined facial features and to produce a signal representative of said facial features; and
   (c) said controller configured to receive said signal and, if said person is recognized from said facial features, to retrieve a stored ocular profile of said reflection and to use said ocular profile for eye tracking while viewing said entire face of said person.

4. An apparatus for eye tracking, as defined in claim 3, wherein: if said person is not recognized, said controller causes said sensor to view only said eye of said person and uses such information to create an ocular profile therefor for use in eye tracking.

5. An apparatus for eye tracking, as defined in claim 1, wherein: all elements of said apparatus operate automatically.

6. An apparatus for eye tracking, as defined in claim 1, wherein: all elements of said apparatus operate without mechanical linkages.

7. An apparatus for eye tracking, as defined in claim 1, wherein: said apparatus uses SXGA resolution.

8. An apparatus for eye tracking, as defined in claim 3, wherein: if said person is not recognized, said controller restricts how a vehicle can be operated and/or restricts access to certain areas of said vehicle.

9. An apparatus for eye tracking, as defined in claim 3, wherein: if contact with said eye is lost, said controller uses said entire face of said person to locate said eye.

* * * * *